United States Patent
Hamid et al.

(10) Patent No.: US 11,715,312 B1
(45) Date of Patent: Aug. 1, 2023

(54) SMART INFORMATION RECOGNITION FOR USER HEALTH IDENTIFICATION THROUGH COVID-19 APPLICATIONS

(71) Applicant: University of Sharjah, Sharjah (AE)

(72) Inventors: Abdul Kadir Hamid, Sharjah (AE); Mena Maurice Farag, Sharjah (AE); Waleed Obaid, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 18/091,759

(22) Filed: Dec. 30, 2022

(51) Int. Cl.
*G06V 30/224* (2022.01)
*G06V 30/148* (2022.01)
*G16H 50/30* (2018.01)
*G06V 30/18* (2022.01)

(52) U.S. Cl.
CPC .......... *G06V 30/224* (2022.01); *G06V 30/148* (2022.01); *G06V 30/18105* (2022.01); *G16H 50/30* (2018.01)

(58) Field of Classification Search
CPC .................................................. G16H 50/30
See application file for complete search history.

(56) References Cited

U.S. PATENT DOCUMENTS

| 11,010,943 B1 * | 5/2021 | Bajic | G06T 7/136 |
| 2020/0193609 A1 * | 6/2020 | Dharur | G06T 7/143 |
| 2021/0296008 A1 | 9/2021 | Novak, Jr. et al. | |

OTHER PUBLICATIONS

Somasekar et al., "Withdrawn: Machine learning and image analysis applications in the fight against COVID-19 pandemic: Datasets, research directions, challenges and opportunities", PMC PubMed Central, National Library of Medicine, Mater Today Proc., 2020, 10.1016/j.matpr.2020.09.352. 1 page.
"WHO Coronavirus (COVID-19) Dashboard | WHO Coronavirus (COVID-19) Dashboard With Vaccination Data." https://covid19.who.int/, website accessed Feb. 10, 2021, 2 pages.
Nishant Renu, "Technological advancement in the era of COVID-19", Sage Open Medicine, 2021, vol. 9, pp. 1-4, 4 pages.
Umair et al., "Impact of COVID-19 on IoT Adoption in Healthcare, Smart Homes, Smart Buildings, Smart Cities, Transportation and Industrial IoT", Sensors, 2021, vol. 22, Issue 3838, 33 pages.

(Continued)

*Primary Examiner* — Edward Park
(74) *Attorney, Agent, or Firm* — Hayes Soloway PC (57) ABSTRACT

A system and a method for smart information recognition for user health identification are disclosed. The system and the method comprise a display unit, a color code detection unit, an image filter, an optical character recognition unit, a code detection unit and an elimination unit. The display unit contains a user information. The color code detection unit is associated with the display unit to split at least one of the user information by analyzing at least three colors in an image. The image filter detects at least one of the user's information. Further, the optical character recognition unit recognizes a text of the user information. The code detection unit detects an image code and the elimination unit is used for eliminating a binary object that is close to an image border. The proposed system and method ensure complete security to prevent abuse of an individual's personal information.

20 Claims, 7 Drawing Sheets

(56) References Cited

OTHER PUBLICATIONS

Seyed Shahim Vedaei et al., "COVID-Safe: An IoT-Based System for Automated Health Monitoring and Surveillance in Post-Pandemic Life", IEEEAccess, Digital Object Identifier, 2020, vol. 8, pp. 188538-188551, 4 pages.

Setti et al., "Airborne Transmission Route of COVID-19: Why 2 Meters/6 Feet of Inter-Personal Distance Could Not Be Enough", PMC PubMed Central, National Library of Medicine, International Journal of Environmental Research and Public Health, 2020, vol. 17, Issue 8: 2932, 6 pages.

Tamar Sharon, "Blind-sided by privacy? Digital contact tracing, the Apple/Google API and big tech's newfound role as global health policy makers", Ethics and Information Technology, 2021, vol. 23(Suppl 1), pp. 45-57, 13 pages.

Utsav et al., "Unique Identification for Monitoring of COVID-19 Using the Internet of Things (IoT)", IEEE Xplore, IEEE International Conference on Computing, Communication and Security (ICCCS), Department of Electronics and Communication, 2020, doi: 10.1109/ICCCS49678.2020.9276769, 5 pages.

Deshpande & Schuller, "An Overview on Audio, Signal, Speech, & Language Processing for COVID-19", ResearchGate, 2020, http://arxiv.org/abs/2005.08579, 5 pages.

Imran et al., "AI4COVID-19: AI enabled preliminary diagnosis for COVID-19 from cough samples via an app", Elsevier, Informatics in Medicine Unlocked, 2020, vol. 20, 13 pages.

Eiko Yoneki, "FluPhone Study: Virtual Disease Spread using Haggle", ACM Digital Library, Chants '11: Proceedings of the 6th ACM workshop on Challenged networks, 2011, pp. 65-66, 2 pages.

Yoneki & Crowcroft, "EpiMap: Towards Quantifying Contact Networks and Modelling the Spread of Infections in Developing Countries", ScienceDirect, Elsevier, Ad Hoc Networks, 2014, vol. 13, Part A, pp. 83-93, 8 pages.

Polenta et al., "An Internet of Things Approach to Contact Tracing—The BubbleBox System", Information, 2020, vol. 11, Issue 7, 12 pages.

Tedeschi et al., "IoTrace: A Flexible, Efficient, and Privacy-Preserving IoT-enabled Architecture for Contact Tracing", IEEE Xplore, IEEE Communications Magazine, 2021, vol. 59, Issue 6, 7 pages.

Gupta, "Enabling and Enforcing Social Distancing Measures using Smart City and ITS Infrastructures: COVID-19 Use Case", ResearchGate, 2020, pp. 1-5, 5 pages.

* cited by examiner

SMART INFORMATION RECOGNITION FOR USER HEALTH IDENTIFICATION THROUGH COVID-19 APPLICATIONS

FIELD OF THE INVENTION

Embodiments of the present invention relate to the field of health monitoring or remote health screening, more particularly relating to a system and a method for smart information recognition for user health identification to avoid the risk of having an infectious disease.

BACKGROUND OF THE INVENTION

Over the past two to three years, the recent global pandemic of the coronavirus disease (COVID-19) has garnered attention on a global scale. To remove the sickness/illness of an infectious disease in the best possible way, all of the nations have been keeping an eye on the global outbreak. The World Health Organization (WHO) estimated worldwide data till Oct. 2021 is 233,504,524.

The recent pandemic opened the chances of digitalization and the exponential rise in the adoption of digital technologies. Because of this digitalization, people have adopted the technology as soon as possible. This digitalization helps people to adopt the technology through various government organizations. Many government entities perform large investments to fight the global pandemic using IoT and other available technologies.

As the pandemic is increasing day by day, many solutions are present in the market like as smart solutions for smart recognition and IoT applications to maintain a safer society-working environment for employees and other individuals in all fields. Some intelligent systems are used in various fields like healthcare, and transportation to reduce the chances of spreading contagious or infectious diseases. Many vaccines are used to protect people from these kinds of diseases.

Many tracking devices are used for tracking people's physical condition through the inspection of a polymerase chain reaction test (PCR) or through the inspection of the symptoms related to the disease that reduce the transmission of infectious diseases.

Some smart systems are available in the market that is used for monitoring the user's health condition by using sensor and QR (quick response) identification code recognition unit. The sensor and QR data are stored in a memory that is easily accessible by the doctors and health representatives in order to provide medications to the user according to their health conditions.

Another approach is to use an audio signal processing system. In these types of systems, it is easy to recognize whether cases are at an advanced level or whether people are facing normal influenza or another type of medical condition. The systems and methods are used for distinguishing the advanced cases of COVID-19 and other medical respiratory conditions through the development of an Artificial Intelligence based model. Furthermore, the user mobile phones have been utilized to collect data related to flu symptoms, and GPS monitoring systems are used for tracking people who have the symptoms.

Another example is US20210296008A1 discloses a system for remotely monitoring and managing the health statuses of a plurality of users including software instructions storable on a memory device usable by a computing device, the software instructions causing a hardware processor of the computing device to receive a plurality of sets of health-related information from a plurality of mobile computing devices of a plurality of users. The health-related information includes physiological information derived from wearable devices of the users indicative of an onset of symptoms associated with an infection, contact tracing data, and diagnosis data. The hardware processor determines exposure levels based on at least the contact tracing data and determines user-specific risk states based on physiological information, diagnosis data, and exposure levels.

But the above-disclosed patent has some disadvantages. The above system does not disclose a color code detection unit and an image filter that helps in splitting at least one of the user information by analyzing at least three colors in an image and detecting at least one of the user information by applying at least two threshold values on each of the at least three colors. The above system only discloses the wearable device that is used for remotely monitoring and managing the health statuses of a plurality of users.

However, such systems and methods have a limited reach among the population, as it requires the use of smartphone devices and wearable devices is a mandatory requirement. Not every person is capable of affording the smartphone and the wearable device. The factor of being affordable is essentially vital considering the COVID-19 pandemic of 2020.

Another disadvantage is the privacy of the user, including the data of the movement and other personal details. These systems are failed in providing data security for the user's personal information. These systems also fail in providing a complete smart process from the scanning process to the validation of results.

In light of the limited reach and user privacy issues of existent solutions, there is a dire need for a cost-effective system that may be used as a solution for the prevention of contagious diseases/epidemics/pandemics through smart information recognition for user health identification associated with COVID-19 pandemic. Further, it is desirable for such a solution to consider the security of the privacy of the user information that is helpful in detecting positive and negative cases and all information about the user.

SUMMARY OF THE INVENTION

An embodiment of the present disclosure relates to a system for smart information recognition for user health identification. The system includes a display unit, a color code detection unit, an image filter, an optical character recognition unit, a code detection unit, and an elimination unit.

In accordance with an embodiment of the present invention, the display unit that is a display screen contains a user information that includes a username, a user Identification number, a test state, a vaccinated state, and a date of the vaccinated state. Further, the test state includes a red state, a green state, and an orange state in which the red state indicates that the user is infected by a virus, the green state indicates that the user is not infected by the virus, and the orange state indicates that the user needs to repeat a virus test.

In accordance with an embodiment of the present invention, the virus is a contagious virus-like COVID-19 virus, but not limited to Tuberculosis, Swine Flu, among others, and the virus test is an RTPCR test.

In accordance with an embodiment of the present invention, the color code detection unit that is an RGB color code detection unit is connected to the display unit for splitting at least one of the user information by analyzing at least three colors in an image. The at least three colors are a red color, a green color, and a blue color, wherein these the at least three colors are known as an RGB color component.

In accordance with an embodiment of the present invention, the image is initially processed by detecting the username and the user Identification numbers ID (like an EID), the next information that is extracted is the vaccination state (whether the user is vaccinated or not) and the date of the vaccinated state (a last negative RTPCR test that was taken).

In accordance with an embodiment of the present invention, the image filter detects at least one of the user information by applying at least two threshold values on each of the at least three colors. Further, the at least two threshold values are a high threshold value and a low threshold value in which the high threshold value is used for eliminating an object with pixels that are less than a pixel threshold number, and the low threshold value that is used for creating a mask for the image. This mask is used with the image that is filtered between the at least two threshold values.

In accordance with an embodiment of the present invention, the at least two threshold values of the red color, the blue color, and the green color are 85 and 255, 0 and 70, and 0 and 90 respectively.

In accordance with an embodiment of the present invention, the optical character recognition unit for recognizing a text of the user information. Further, the code detection unit for detecting an image code by combining at least two operations that are an image thresholding operation and an image morphological operation.

In accordance with an embodiment of the present invention, the elimination unit for eliminating a binary object that is close to an image border. Further, the image code is any one of a QR code, a scanning code, a 2D barcode, or a Maxi Code, among others.

Another embodiment of the present disclosure relates to a method for smart information recognition for user health identification. The method includes a display unit, a color code detection unit, an image filter, an optical character recognition unit, a code detection unit, and an elimination unit to perform multiple steps.

In accordance with an embodiment of the present invention, in the first step, the display unit that is a display screen displays a user information that includes a username, a user Identification number, a test state, a vaccinated state, and a date of the vaccinated state. In the next step, the color code detection unit is associated with the display unit for splitting at least one of the user information by analyzing at least three colors in an image in which the at least three colors are a red color, a green color, and a blue color, wherein these the at least three colors are known as an RGB color component. In the third step, the image filter detects at least one of the user information by applying at least two threshold values on each of the at least three colors. Further, the at least two threshold values are a high threshold value and a low threshold value, wherein the high threshold value is used for eliminating an object with pixels that are less than a pixel threshold number, and the low threshold value that is used for creating a mask for the image. In the next step, the optical character recognition unit recognizes a text of the user information. In the next step, the code detection unit detects an image code by combining at least two operations, and in the last step, the elimination unit is used for eliminating a binary object that is close to an image border.

The foregoing objectives of the present invention are to provide a feasible method of the user health information extraction through the RGB color code detection unit, which is compatible with hardware to determine the health status of an individual and to ensure the complete security of an individual's personal information so that any kind of data abuse is prevented.

BRIEF DESCRIPTION OF THE DRAWINGS

So that the manner in which the above recited features of the present invention is be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

ELEMENT LIST

Display Unit 102
Color Code Detection Unit 104
Image Filter 106
Optical Character Recognition Unit 108
Code Detection Unit 110
Elimination Unit 112

DETAILED DESCRIPTION

The present invention relates a system for smart information recognition for user health identification. The system helps in extracting a user information to detect a positive or negatives cases of diseases. This system ensures complete security to prevent abuse of user's personal information. Furthermore, importance of information detection unit with hardware compatibility is taken into account to ensure a complete smart process from scanning process to validation of results.

The principles of the present invention and their advantages are best understood by referring to FIG. 1 to FIG. 7. In the following detailed description of illustrative or exemplary embodiments of the disclosure, specific embodiments in which the disclosure may be practiced are described in sufficient detail to enable those skilled in the art to practice the disclosed embodiments.

The following detailed description is, therefore, not to be taken in a limiting sense, and the scope of the present disclosure is defined by the appended claims and equivalents thereof. References within the specification to "one embodiment," "an embodiment," "embodiments," or "one or more embodiments" are intended to indicate that a particular feature, structure, or characteristic described in connection with the embodiment is included in at least one embodiment of the present disclosure.

Figure 1:
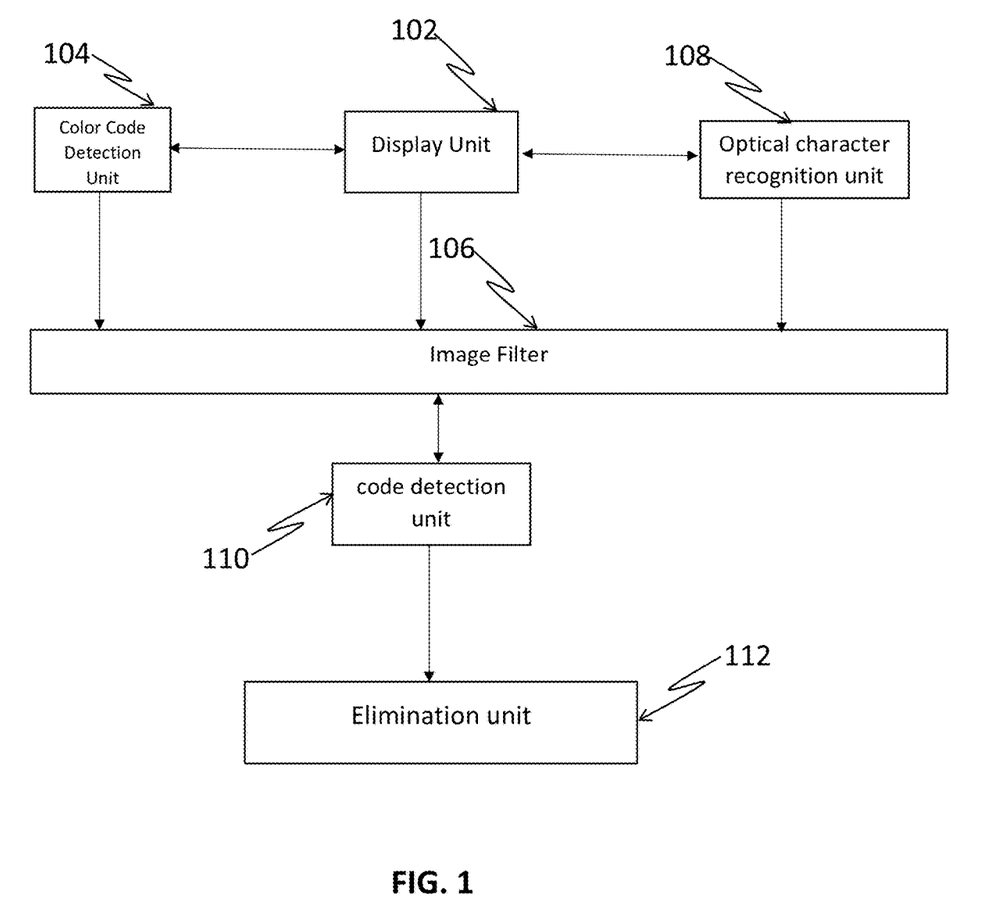
FIG. 1 depicts a perspective view of a system for smart information recognition for user health identification, according to an embodiment of a present invention.

FIG. 1 depicts a perspective view of a system (100) for smart information recognition for user health identification, according to an embodiment of a present invention. The system (100) includes a display unit (102), a color code detection unit (104), an image filter (106), an optical character recognition unit (108), a code detection unit (110), and an elimination unit (112).

In accordance with an embodiment of the present invention, the display unit (102) contains a user information. Further, the display unit (102) is a display screen that is anyone of an LCD (Liquid Crystal Display) screen or an LED (Light Emitting Diodes) screen. Further, the user information includes a username, a user Identification number, a test state, a vaccinated state, and a date of the vaccinated state. Further, the test state includes a red state, a green state, and an orange state in which the red state indicates that the user is infected by a virus, the green state indicates that the user is not infected by the virus, and the orange state indicates that the user needs to repeat a virus test.

In accordance with an embodiment of the present invention, the virus is a contagious virus-like COVID-19 virus, but not limited to Tuberculosis, Swine Flu, among others, and the virus test is an RTPCR (Reverse Transcription-Polymerase Chain Reaction) test.

In accordance with an embodiment of the present invention, the color code detection unit (104) that is an RGB color code detection unit that is connected to the display unit (102) for splitting at least one of the user information by analyzing at least three colors in an image. The at least three colors are a red color, a green color, and a blue color, wherein these the at least three colors are known as an RGB color component.

In the present embodiment, the RGB color detection unit (102) includes an RGB color space that is represented by using a 24-bit implementation. Each channel of the at least three colors have 8 bits. The range of values for each channel is between 255 and 0. The main concept in it is that the colors are directly related to different shades of the red, green, and blue color. The RGB color space combines a chromatic and a luma component which causes it to be very sensitive to noise. In this case, an HSV color space is used to represent the RGB color space.

The HSV refers to three different aspects: hue, saturation, and value. It is considered the human vision concept. The ranges of these 3 components are 360 to 0 for the hue, 100 to 0 for the saturation, and 255 to 0 for the value.

In accordance with an embodiment of the present invention, the RGB and the HSV color spaces are related by some equations. Initially, the RGB components are normalized by the maximum intensity value as follows:

$$R'=R/255, G'=G/255, B'=B/255 \tag{1}$$

Each normalized channel component is processed by selection of maximum and minimum for the normalized channels:

$$Cmax=\max(R',G',B'), Cmin=\min(R',G',B') \tag{2}$$

where both a Cmax and a Cmin correspond to the maximum and minimum respectively. The difference between the maximum and the minimum is obtained afterwards:

$$\Delta=Cmax-Cmin \tag{3}$$

where $\Delta$ is the difference between the extreme values. The Hue is zero if the difference is zero. The Hue is determined based on the Cmax in three cases: when the Cmax is equal to the normalized red color channel, when the Cmax is equal to the normalized green color channel, and when Cmax is equal to the normalized blue color channel as follows:

$$H=0°, \text{ when } \Delta=0$$

$$H=60°\{(G'-B'/\Delta) \bmod 6\}, \text{ when } Cmax=R'$$

$$H=60°\{(B'-R'/\Delta)+2\}, \text{ when } Cmax=G' \tag{4}$$

$$H=60°\{(R'-G')/\Delta)+4\}, \text{ when } Cmax=B'$$

The saturation component is equal to zero or $\Delta$ divided by the Cmax depending on the Cmax:

$$S=0, \text{ when } Cmax=0$$

$$S=\Delta/Cmax, \text{ when } Cmax=/=0 \tag{5}$$

The component value is equals to the Cmax:

$$V=Cmax \tag{6}$$

Figure 2:
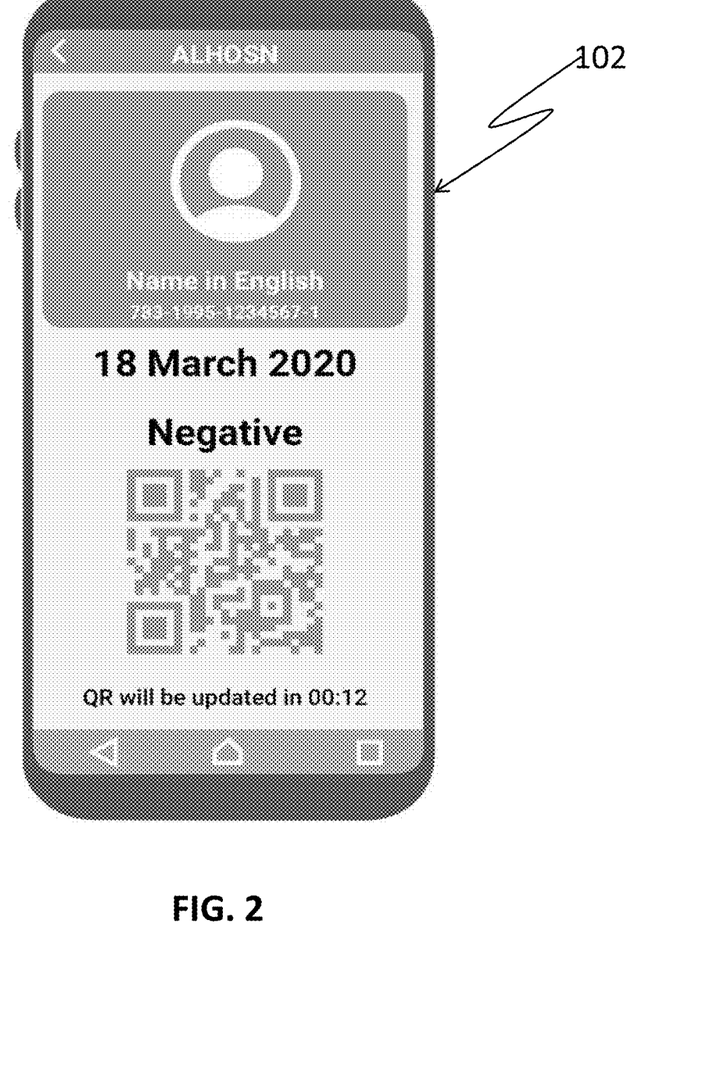
FIG. 2 shows an exemplary embodiment of a display unit that displays the user information after the user successfully logs in to an application of the system.

FIG. 2 shows an exemplary embodiment of the display unit (102) (refer FIG. 1) that displays the user information after the user successfully logs in to an application of the system (100). The display screen (102) (refer FIG. 1) displays the username, user identification number, the date when the user is vaccinated, the test state, and a QR code.

Figure 3:
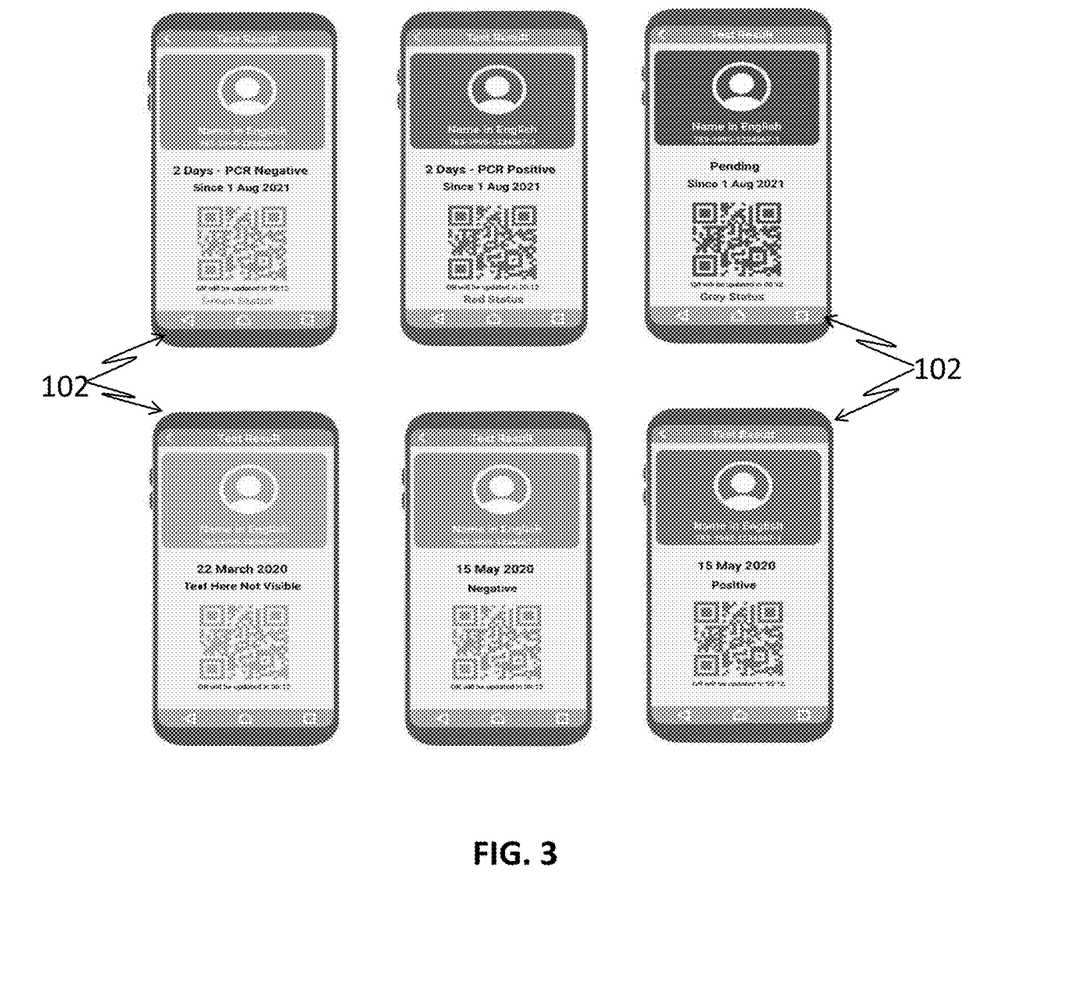
FIG. 3 shows the results of applying at least two threshold values on an image for determining the different test states in accordance with an embodiment of the present invention.

FIGS. 3 shows the results of applying at least two threshold values on an image for determining the different test states in accordance with an embodiment of the present invention. The red state refers to a positive RT PCR test and the orange state is for the requirement of repeating the test. Both states have been detected easily. Further, the green state indicates that the user is not infected by the virus. The blue color indicates the pending status of the test state.

In accordance with an embodiment of the present invention, the image filter (106) detects at least one of the user information by applying at least two threshold values on each of the at least three colors. Further, the at least two threshold values are a high threshold value and a low threshold value in which the high threshold value is used for eliminating an object with pixels that are less than a pixel threshold number and the low threshold value that is used for creating a mask for the image. This mask is used with the image that is filtered between the at least two threshold values.

In accordance with an embodiment of the present invention, the at least two threshold values of the red color, the blue color, and the green color are 85 and 255, 0 and 70, and 0 and 90 respectively.

Figure 4:
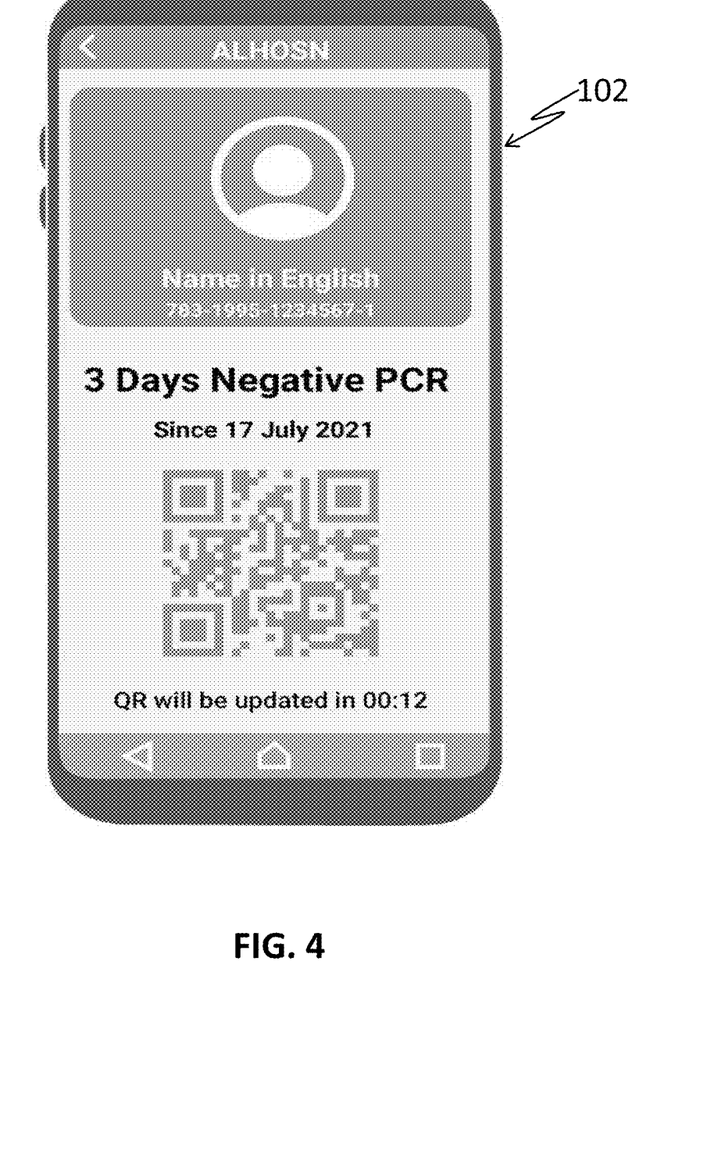
FIG. 4 shows an exemplary embodiment that presents the resultant image after applying an optical character recognition unit, according to an embodiment of the present invention.

FIG. 4 shows an exemplary embodiment that present the resultant image after applying an optical character recognition unit (108) (refer FIG. 1), according to an embodiment of the present invention. Further, the optical character recognition unit (108) is used for recognizing a text of the user information.

In accordance with an embodiment of the present invention, the image is initially processed by detecting the username and the user Identification numbers ID (like an EID), the next information that is extracted is the vaccination state (whether the user is vaccinated or not) and the date of the vaccinated state (a last negative RTPCR test that was taken).

Figure 5:
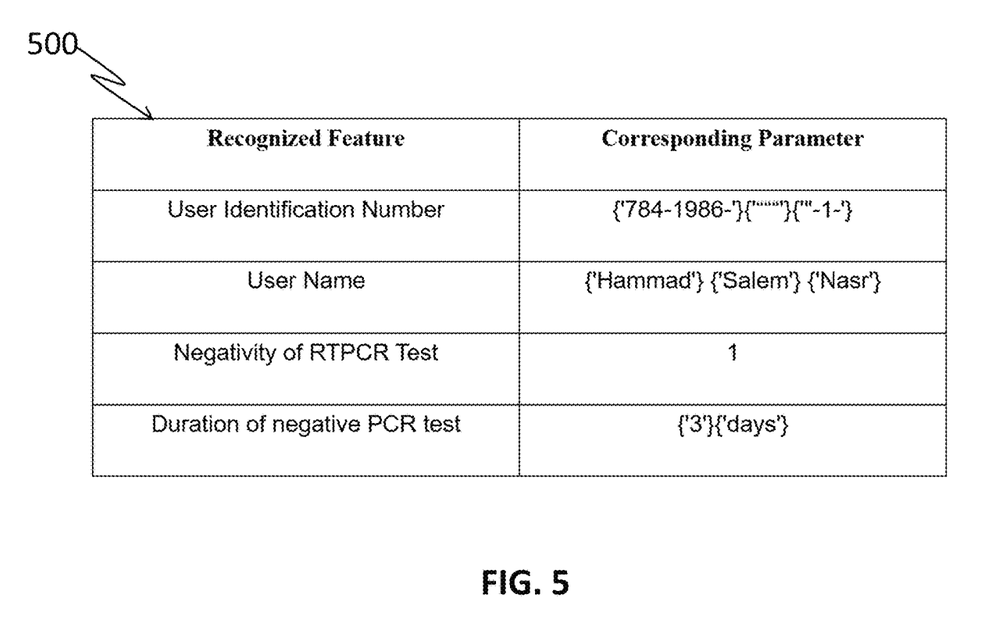
FIG. 5 is a table of the exemplary resulting image, which is illustrated in FIG. 4, according to an embodiment of the present invention.

FIG. 5 is a table 500 of the exemplary resulting image, which is illustrated in FIG. 4, according to an embodiment of the present invention. The table includes a recognized feature and a corresponding parameter. If the recognized feature is the user identification number then the corresponding parameter is {'784-1986-'} {'"'} {"—1—"}. If the recognized feature is the username, then the corresponding parameter is {'Hammad'} {'Salem'} {'Nasr'}. If the recognized feature is the negativity of the RTPCR test, then the corresponding parameter is 1. If the recognized feature is the duration of negativity of the RTPCR test then the corresponding parameter is {'3'} {'days'}.

In accordance with an embodiment of the present invention, in order to detect the vaccination state, the words 'Vaccinated', 'vacc', 'Vacc', and 'vaccinated' are searched throughout the image. For detecting the username and user identification number, the words 'result', 'EID:', and 'PPN' are searched throughout the image. The EID is an Enrollment ID of the user that is the same as the user identification number. The PPN is a preferred provider number. The name is extracted by detecting the words between 'result' and 'EID'. The EID is obtained by detecting the sequence between 'EID' and 'PPN'. The date since the last PCR test is extracted by searching after the word 'Since'.

Further, the code detection unit (110) (refer FIG. 1) for detecting an image code by combining at least two operations that are an image thresholding operation and an image morphological operation. Further, the image code is any one of the QR codes, a scanning code, a 2D barcode, or a Maxi Code, among others.

In accordance with an embodiment of the present invention, the image thresholding operation is a simple form of image segmentation. It is a way to create a binary image from a grayscale or full-color image. This is typically done in order to separate "object" or foreground pixels from background pixels to aid in the image processing.

In accordance with an embodiment of the present invention, the image morphological operation is applied to a broad set of image processing operations that process the images based on their shapes. The morphological operations apply a structuring element to an input image, creating an output image of the same size.

In accordance with an embodiment of the present invention, the input image is first converted from an RGB image to the grayscale image. The next step is applying the high threshold value on the image and eliminating objects with pixels that are less than a threshold number of pixels. The following step is finding the binary inverse of the resultant image and using this inverse as the mask to the gray image. The resultant image is filtered between two threshold values and filtered using a Gaussian filter afterward.

In accordance with an embodiment of the present invention, the gaussian filtering is considered a 2-dimensional convolution. The usage of this filtering includes smoothing images in order to eliminate noise concentrations.

In accordance with an embodiment of the present invention, if the image w (x, y) exists with m x n size, the convolution f (x, y) is performed by w (x, y) * f (x, y) as follows:

$$w(x, y) * f(x, y) = \Sigma\Sigma w(s,t) f(x-s, y-t) \quad b\ t=-b\ a\ s=-a \quad (7)$$

Where a and b are $$a=(m-1)/2 \text{ and}$$

$$b=(n-1)/2.$$

The function f (x, y) is the Gaussian distribution that is as given as follows:

$$f(x, y) = 1/2\pi\sigma [e^{-\{(x^2+y^2)/2\sigma^2\}}] \quad (8)$$

The Gaussian Filter has dimensions besides the standard deviation σ. If σ is large value, smoothing would be more.

Figure 6:
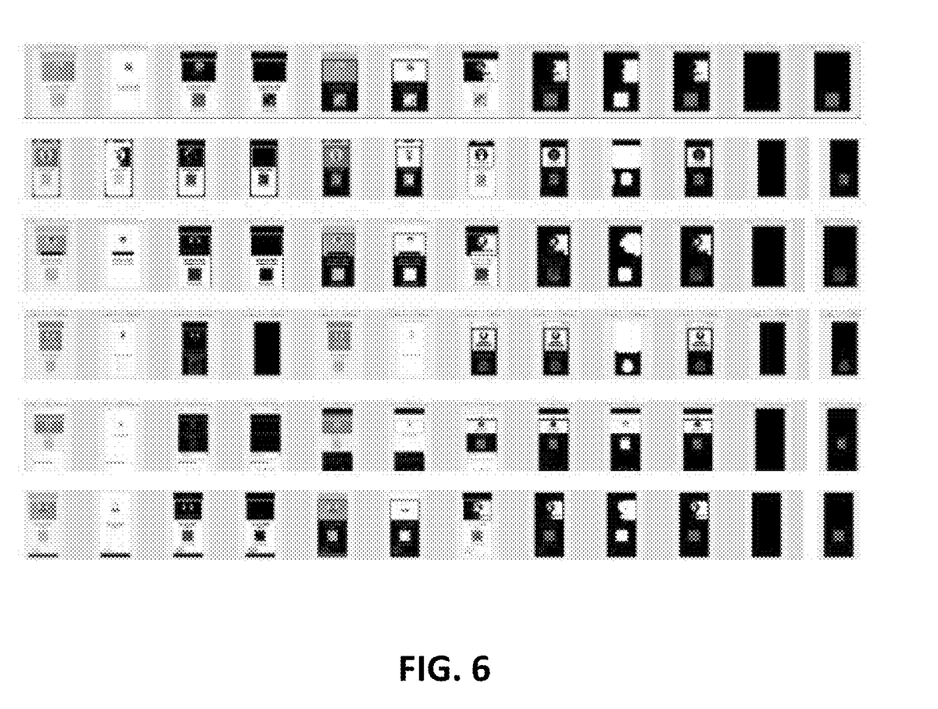
FIG. 6 shows the results of a code detection unit on the different APP images, according to an embodiment of the present invention.

FIG. 6 shows the results of the code detection unit (110) (refer FIG. 1) on the different APP images, according to an embodiment of the present invention. The low threshold value is used for creating a mask for the image. This mask is used with the image that is filtered between two threshold values.

In accordance with an embodiment of the present invention, the elimination unit (112) (refer FIG. 1) is used for eliminating a binary object that is close to an image border. Through this process, the user may get a clear image.

The computer-implemented method 700 is described below, for ease of reference, as being executed by exemplary devices and components introduced with the embodiments illustrated in FIGS. 1-6. For example, the steps of the computer-implemented method 700 may be performed by the mobile electronic devices alone or in conjunction with the backend server, communication server, and/or communication links through the utilization of processors, transceivers, hardware, software (such as the ALHOSN software application and software application described herein), firmware, or combinations thereof. However, a person having ordinary skill will appreciate that responsibility for all or some of such actions may be distributed differently among such devices or other computing devices without departing from the spirit of the present invention.

One or more computer-readable medium(s) may also be provided. The computer-readable medium(s) may include one or more executable programs, such as a MATLAB application and a backend software application ALHOSN, stored thereon, wherein the program(s) instruct one or more processing elements to perform all or certain of the steps outlined herein. The program(s) stored on the computer-readable medium(s) may instruct the processing element(s) to perform additional, fewer, or alternative actions, including those discussed elsewhere herein.

Figure 7:
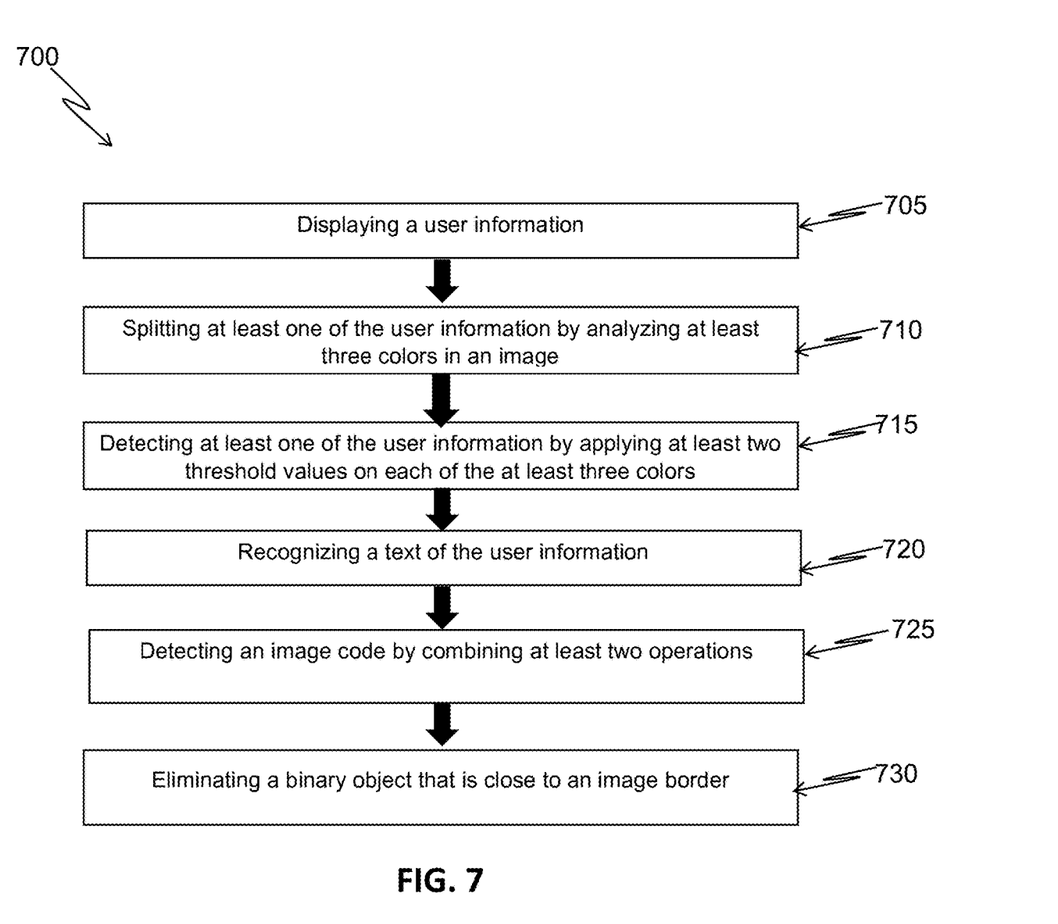
FIG. 7 is a flow chart illustrating a method for smart information recognition for user health identification in accordance with an embodiment of the present invention.

FIG. 7 is a flow chart illustrating a method (700) for smart information recognition for user health identification in accordance with an embodiment of the present invention. The method (700) includes a display unit (102) (refer FIG. 1), a color code detection unit (104), an image filter (106), an optical character recognition unit (108), a code detection unit (110), and an elimination unit (112) to perform multiple steps.

In accordance with an embodiment of the present invention, the method (700) starts from step (705) in which the display unit (102) that is a display screen displays a user information. Further, the user information includes a username, a user Identification number, a test state, a vaccinated state, and a date of the vaccinated state.

In accordance with an embodiment of the present method (700), the test state includes a red state, a green state, and an orange state in which the red state indicates that the user is infected by a virus, the green state indicates that the user is not infected by the virus, and the orange state indicates that the user needs to repeat a virus test.

In accordance with an embodiment of the present method, the virus is a contagious virus-like COVID-19 virus, but not limited to Tuberculosis, Swine Flu, among others, and the virus test is an RTPCR (Reverse Transcription-Polymerase Chain Reaction) test.

Step (705) proceeds to step (710). At step (710), the color code detection unit (104) (refer FIG. 1) is associated with the display unit (102) for splitting at least one of the user information by analyzing at least three colors in an image. The color code detection unit (104) is an RGB color code detection unit and the at least three colors are a red color, a green color, and a blue color, wherein the at least three colors are known as an RGB color component.

Step (710) proceeds to step (715). At step (715), the image filter (106) detects at least one of the user information by applying at least two threshold values on each of the at least three colors. Further, the at least two threshold values are a high threshold value and a low threshold value, wherein the high threshold value is used for eliminating an object with pixels that are less than a pixel threshold number and the low threshold value that is used for creating a mask for the image.

Step (715) proceeds to step (720). At step (720), the optical character recognition unit (108) recognizes a text of the user information. Step (720) proceeds to step (725). At step (725), the code detection unit (110) detects an image code by combining at least two operations. Further, the at least two operations are an image thresholding operation and an image morphological operation. Further, the image code is any one of a QR code, a scanning code, a 2D barcode, or a Maxi Code, among others.

Step (725) proceeds to step (730). At step (730), the elimination unit is used for eliminating a binary object that is close to an image border.

In accordance with an advantageous embodiment of the present invention, the system (100) and the method (700) provide a feasible extraction of the user information that helps in determining the health information of the user. Further, the optical character recognition unit (108) helps in extracting the user-associated information such as national identity and Covid-19 Virus State. This system (100) is a cost-effective system and is compatible with the hardware. Data transparency is considered in such system (100) for maintaining the confidentiality of the user information. This system (100) is expanded to multiple applications and institutes that require smart information recognition for its users.

In an alternative embodiment, a plurality of sensors may be installed with the code detection unit (110) and the RGB color code detection unit (104) that ensures the plausible reduction in possible face-to-face contact between security personnel and individuals upon inspection of COVID-19 APP information. Such implementation with hardware would ensure validation detection results through a hardware mechanism that allows individuals to access places that require the RTPCR negative or the vaccinated test results.

In another alternative embodiment, the present invention may combine with an IoT-based devices. The devices are intended but not limited to a wristband or a detachable tag attached to a tracing object. The devices are able to communicate among themselves and exchange their unique identification ID, and the user information (like the username, user ID, test, and vaccinated state). The IoT-enabled devices will serve as nodes to send the stored information on the devices to a central server, and vice-versa.

It should be noted that the invention has been described with reference to particular embodiments and that the invention is not limited to the embodiments described herein.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

The invention claimed is:

1. A system for smart information recognition for user health identification, comprising:
    a display unit that contains a user information;
    a color code detection unit associated with the display unit for splitting at least one of the user information by analyzing at least three colors in an image;
    an image filter for detecting at least one of the user information by applying at least two threshold values on each of the at least three colors, wherein the at least two threshold values are a high threshold value and a low threshold value, wherein the high threshold value is used for eliminating an object with pixels that are less than a pixel threshold number and the low threshold value that is used for creating a mask for the image;
    an optical character recognition unit for recognizing a text of the user information;
    a code detection unit for detecting an image code by combining at least two operations; and
    an elimination unit for eliminating a binary object that is close to an image border.

2. The system as claimed in claim 1, wherein the user information includes a username, a user Identification number, a test state, a vaccinated state, and a date of the vaccinated state.

3. The system as claimed in claim 2, wherein the test state includes a red state, a green state, and an orange state.

4. The system as claimed in claim 3, wherein the red state indicates that the user is infected by a virus, the green state indicates that the user is not infected by the virus, and the orange state indicates that the user needs to repeat a virus test.

5. The system as claimed in claim 4, wherein the virus is a contagious virus-like COVID-19 virus and the virus test is an RTPCR test.

6. The system as claimed in claim 1, wherein the at least three colors are a red color, a green color, and a blue color, wherein these the at least three colors are known as an RGB color component.

7. The system as claimed in claim 1, wherein the at least two threshold values of the red color, the blue color, and the green color are 85 and 255, 0 and 70, and 0 and 90 respectively.

8. The system as claimed in claim 1, wherein the at least two operations are an image thresholding operation and an image morphological operation.

9. The system as claimed in claim 1, wherein the image is initially processed by detecting the username and the user Identification numbers ID (like an EID), the next information that is extracted is the vaccination state (whether the user is vaccinated or not) and the date of the vaccinated state (a last negative RTPCR test that was taken).

10. The system as claimed in claim 1, wherein the mask is used with the image that is filtered between the at least two threshold values.

11. The system as claimed in claim 1, wherein the image code is any one of a QR code, a scanning code, a 2D barcode, or a Maxi Code, among others.

12. The system as claimed in claim 1, wherein the display unit is a display screen and the color code detection unit is an RGB color code detection unit.

13. A method for smart information recognition for user health identification, comprising:
   displaying, by a display unit, a user information;
   splitting, by a color code detection unit associated with the display unit, at least one of the user information by analyzing at least three colors in an image;
   detecting, an image filter, at least one of the user information by applying at least two threshold values on each of the at least three colors, wherein the at least two threshold values are a high threshold value and a low threshold value, wherein the high threshold value is used for eliminating an object with pixels that are less than a pixel threshold number and the low threshold value that is used for creating a mask for the image;
   recognizing, by an optical character recognition unit, a text of the user information;
   detecting, by a code detection unit, an image code by combining at least two operations; and
   eliminating, by an elimination unit, a binary object that is close to an image border.

14. The method as claimed in claim 13, wherein the user information includes a username, a user Identification number, a test state, a vaccinated state, and a date of the vaccinated state.

15. The method as claimed in claim 14, wherein the test state includes a red state, a green state, and an orange state.

16. The method as claimed in claim 15, wherein the red state indicates that a user is infected by a virus, the green state indicates that the user is not infected by the virus, and the orange state indicates that the user needs to repeat a virus test.

17. The method as claimed in claim 16, wherein the virus is a contagious virus-like COVID-19 virus, and the virus test is an RTPCR test.

18. The method as claimed in claim 13, wherein the at least three colors are a red color, a green color, and a blue color, wherein these the at least three colors are known as an RGB color component.

19. The method as claimed in claim 13, wherein the image is initially processed by detecting the username and the user Identification numbers ID (like an EID), the next information that is extracted is the vaccination state (whether the user is vaccinated or not) and the date of the vaccinated state (a last negative RTPCR test that was taken).

20. The method as claimed in claim 13, wherein the image code is any one of a QR code, a scanning code, a 2D barcode, or a Maxi Code, and wherein the display unit is a display screen, and the color code detection unit is an RGB color code detection unit.

\* \* \* \* \*